US011435331B2

(12) United States Patent
McNulty et al.

(10) Patent No.: US 11,435,331 B2
(45) Date of Patent: Sep. 6, 2022

(54) ADAPTIVE SENSING SYSTEM FOR AMBIENT GROUND-GAS CONCENTRATION AND FLOW-RATE MEASUREMENT

(71) Applicant: AMBISENSE LTD., Dublin (IE)

(72) Inventors: Stephen McNulty, Dublin (IE); Fiachra Collins, Dublin (IE)

(73) Assignee: AMBISENSE LTD., Dublin (IE)

( * ) Notice: Subject to any disclaimer, the term of this patent is extended or adjusted under 35 U.S.C. 154(b) by 296 days.

(21) Appl. No.: 16/340,042

(22) PCT Filed: Oct. 5, 2017

(86) PCT No.: PCT/EP2017/075405
§ 371 (c)(1),
(2) Date: Apr. 5, 2019

(87) PCT Pub. No.: WO2018/065544
PCT Pub. Date: Apr. 12, 2018

(65) Prior Publication Data
US 2020/0064319 A1     Feb. 27, 2020

(30) Foreign Application Priority Data
Oct. 5, 2016    (EP) .................................... 16192460

(51) Int. Cl.
*G01N 33/00*     (2006.01)
*G01F 15/00*     (2006.01)
(Continued)

(52) U.S. Cl.
CPC ......... *G01N 33/004* (2013.01); *G01F 15/005* (2013.01); *G01L 9/00* (2013.01);
(Continued)

(58) Field of Classification Search
CPC ............. G01N 33/004; G01N 33/0044; G01N 33/0047; G01N 33/0075; G01N 33/0022;
(Continued)

(56) References Cited

U.S. PATENT DOCUMENTS

| 5,223,783 A * | 6/1993 | Wilis ................. G01N 33/0026 |
| | | 204/409 |
| 6,169,962 B1 | 1/2001 | Brookshire et al. |

(Continued)

OTHER PUBLICATIONS

Ambisense Ltd: "Autonomous Monitoring Technology" Retrieved from the Internet <URL:http://www.ambisense.net/ckeditor uploads/files/AmbiSense Brochure Feb15.pdf> [retrieved on Feb. 21, 2017].

*Primary Examiner* — David L Singer
*Assistant Examiner* — Fatemeh Esfandiari Nia
(74) *Attorney, Agent, or Firm* — Loza & Loza, LLP; Anthony G. Smyth (57) ABSTRACT

A gas sensing device has a power source, data processing means and a memory for storing sampling configuration data and sensed data. Sensing means samples ambient gas adjacent the device according to first sampling configuration data and outputs sensed gas concentration data and sensed gas flow data. A telemetry module communicates the sensed data to a remote terminal and receives second sampling configuration data from the remote terminal for updating the first sampling configuration data. A gas monitoring system comprises the terminal and at least one gas sensing device remote from the terminal. The sampling configuration data comprises data representative of a frequency and duration of gas flow measurement, data representative of a frequency and duration of gas concentration measurement, and data representative of an offset time corresponding to a time interval between a gas flow measurement and a gas concentration measurement.

10 Claims, 6 Drawing Sheets

(51) Int. Cl.
  *G01L 9/00*   (2006.01)
  *G01N 1/24*   (2006.01)
  *H02S 99/00*  (2014.01)
  *E21B 43/00*  (2006.01)

(52) U.S. Cl.
  CPC .......... *G01N 1/24* (2013.01); *G01N 33/0044* (2013.01); *G01N 33/0047* (2013.01); *H02S 99/00* (2013.01); *E21B 43/00* (2013.01)

(58) Field of Classification Search
  CPC .......... G01N 1/24; G01F 15/005; G01L 9/00; H02S 99/00; Y02E 10/50
  See application file for complete search history.

(56) References Cited

U.S. PATENT DOCUMENTS

| | | | |
|---|---|---|---|
| 10,029,291 B2 * | 7/2018 | Fischer | E21B 43/12 |
| 2001/0005812 A1 * | 6/2001 | Brookshire | B09B 1/00 |
| | | | 702/6 |
| 2013/0275047 A1 * | 10/2013 | Selman | E21B 49/005 |
| | | | 702/9 |
| 2015/0052975 A1 * | 2/2015 | Martin | F24F 11/30 |
| | | | 73/31.02 |
| 2016/0238494 A1 * | 8/2016 | Chrin, II | G05D 7/0635 |
| 2017/0218730 A1 * | 8/2017 | Campanella | E21B 43/00 |

\* cited by examiner

ADAPTIVE SENSING SYSTEM FOR AMBIENT GROUND-GAS CONCENTRATION AND FLOW-RATE MEASUREMENT

CROSS-REFERENCE TO RELATED APPLICATIONS

This application is the U.S. National Stage of International Patent Application No. PCT/EP2017/075405 filed on Oct. 5, 2017, which claims the benefit of priority from EP Patent Application No. 16192460.0 filed Oct. 5, 2016, the disclosures of the foregoing applications being incorporated herein by reference in their entirety for all applicable purpose.

FIELD

The present invention relates to gas sensing devices and systems. More particularly, the present invention relates to systems and sensing devices for detecting ambient ground gas concentrations and flow rates in an environment for risk assessment and quantification purposes.

BACKGROUND

Ground gases are those gases generated in the soil pore structure by processes such as biodegradation of organic materials or chemical reactions, whether in natural contexts such as marshlands, peat bogs and in areas of chalky and limestone, or in artificial contexts such as waste landfills and other industrious processes including oil and gas extraction, mining, manufacturing, forestry, agriculture and more. Ground gases are therefore referred under various names or types, such as landfill gas, soil gas, soil vapours, depending upon the context in which they arise. Ground gases are known constitute a risk to human health and safety, and are significant environmental pollutants, whereby their accurate measurement is required as an integral part of many industrial and environment control processes.

It has long been known to measure landfill gases emitted by decomposing waste which, buried in landfills, degrades in anaerobic conditions and produces non-trivial volumes of methane and carbon dioxide in a ratio of 50:50 to 60:40. Skilled persons have harnessed the elevated calorific value conferred to landfill gas by its methane contents, with techniques developed to gather landfill gas by suction, having gas extraction rates typically ranging from 25 to 10,000 m$^3$/hr, and then processing same into electricity, heat, fuels and various chemical compounds.

Improvements in the quality, accuracy and periodicity of measurements in landfill gas monitoring techniques are primarily driven by the economical throughput requirements of landfill gas processing applications: given the natural and somewhat unpredictable composition of waste, the quality of landfill gas defined by its methane contents varies over time, whereby the supply of landfill gas to a turbine or other calorific converter must therefore be adjusted accordingly for maintaining an optimal conversion rate. The traditional industry practice of operators periodically traversing landfill sites with handheld monitoring equipment, and adjusting valves at landfill gas wells based on equipment readings, a technique known as 'field balancing', is a highly inefficient process: there are usually so many landfill gas wells on a landfill site, that the rate of variation in the landfill gas composition exceeds the rate at which the operator can measure the calorific value and perform timely adjustments across all wells of the site. For this reason, techniques have been developed to automate field balancing.

US 2016/238494 is a first example of a solution for automating filed balancing in a landfill site, with a gas monitoring and control system including a gas sampling chamber, sampling inlet and outlet valves, a pump and a controller, wherein sensors are disposed within the chamber that sense characteristics of a gas and generate representative signals, and wherein the controller causes the sampling inlet and outlet valves, and the pump to alternate operating in a gas sampling or purge state to selectively expose the sensors to the gas and purge the chamber with ambient air. This system periodically samples landfill gas and actuates a valve based on the gas quality, but does not measure the gas flow-rate.

U.S. Pat. No. 6,169,962 is a second example of a solution for automating filed balancing in a landfill site, with a computer-controlled landfill gas recovery system associating vaults with one or more landfill wells, wherein each vault includes a shielded enclosure that holds sensors and a local vault controller for generating signals representative of flow rate, vacuum, and oxygen/methane/carbon dioxide content of the gas being extracted from the well, and wherein the wells are in fluid communication with a piping system located in the associated vault, the piping system including a main pneumatic control valve that can be adjusted to establish gas flow rate through the well or wells according to the generated signals. This system periodically samples landfill gas and adjusts a pneumatic valve to set a fixed flow rate or to minimise oxygen contents of the landfill gas.

However, gas monitoring techniques specifically developed for landfill gas applications are of very limited relevance when considering the requirement for passively monitoring ground gases in ambient conditions, outside of such highly anaerobic environments as landfills. This lack of relevance is explained by the fundamental differences between ambient ground gas, which vents passively from the soil, and landfill gas, which is actively extracted. Physical parameters, such as typical volumes and flow rates, vary by several orders of magnitude between ambient ground gas monitoring (typically, $7^{-5}$ to 0.07 m$^3$/hr$^1$) and landfill gas monitoring (typically, 25 to 10,000 m$^3$/hr). As noted, the type of extraction process being measured by ground gas monitoring is passive, in opposition to the active extraction process measured by landfill gas monitoring. While the chemical composition of landfill gas fluctuates as waste degrades, this fluctuation is more trivial in ambient ground gas, the physical properties of which, as pressure and flow-rate, vary considerably with atmospheric and site conditions; thus the fluctuant properties measured by ground gas monitoring are physical, consisting of flow rate, pressure and temperature, whereas those measured by landfill gas monitoring are chemical, consisting of methane and/or oxygen concentration. The causes of fluctuations in ambient ground gas concentration are atmospheric and generally site-specific, whereas those in landfill gas hinge upon the rate of degradation of waste. Economically, the reasons for monitoring ambient ground gas are risk compliance and risk-respective whereas those for monitoring landfill gas are to maximise processing efficiency.

http://www.nhbc.co.uk/NHBCpublications/LiteratureLibrary/Technical/filedownload.29440.en.pdf Accordingly the design of monitoring and control systems for ambient ground gas context is very different. An example context for ambient ground gas monitoring is provided by recent legislation governing risk assessment procedures for geographical site redevelopment, of which the measurement of ground-gas concentrations and flows is intrinsic, and accordingly included in normative guidelines such as "BS 8485:2015 Code of practice for the design of protective measures for methane and carbon dioxide ground gases for new buildings" published by the British Standard Institute. Ambient ground gas monitoring is typically performed as part of site investigation and remediation processes in the contaminated land industry, as a risk assessment to determine either the likelihood of vapour intrusion into any proposed overlying buildings, which would represent a permanent health and environmental risk therein, or the factuality of off-site vapour migration. The risk assessment measures both the toxicity of ambient ground gas and its flow-rate, to determine the likelihood and severity of any gas migration or intrusion. In the contaminated land industry, the risk assessment results are used to engineer gas protection measures for protecting human health, and the difference between a high ambient ground gas risk and a low risk represents significant additional costs to a residential or industrial construction project.

The accurate measurement of ambient ground gases requires both the measurement of ambient ground gas concentration, to determine the constituent elements of gases that are present in a given sample, and the measurement of gas flow, to determine the quantity of ambient ground gases present and its fluidic motion. The fluidic behaviour of ambient ground gas impedes the measurement accuracy, because ambient ground gas is heavily affected by meteorological variations, for instance atmospheric pressure, air temperature and local wind conditions, besides different specific characteristics of an environment, such as moisture or water level, soil type and more. Because ambient ground gas flow-rates are low magnitude, they are highly sensitive to the aforementioned meteorological and environment variations. Furthermore, the veracity of readings attained are substantially influenced by the choice of device and selection of manual technique employed.

Ambient ground gases are measured typically from specifically constructed boreholes drilled into the ground strata. Subterranean perforated sections within the well structure allow for the temporary capture of ground-gas flux, where a representation sample of this volume is extracted upwards via a sampling tap in the sealed headspace at the surface. The state of sealing of this headspace, the density composition of the ground-gases and the interim time between samples have a significant influence on the gas flow-rates.

The fluidic behaviour of ground gas is thus highly fluctuant, whereby continuous high frequency gas monitoring is an optimised technique for accurately measuring, understanding and predicting ground gas behaviour. A number of prior art solutions exist, which facilitate high frequency monitoring of ground gas concentrations.

WO 2007/141512 discloses a typical self-contained gas monitoring apparatus comprising a detector for measuring a gas variable, and a controller configured to automatically and periodically use the detector to measure a gas variable.

US 2012/229287 discloses a system for monitoring the amount of a selected gas in a gas flow, with a gas sensor for sensing the selected gas in the gas flow and producing a corresponding electrical signal, at least one pressure regulator to adjust a pressure of the gas flow to a standardized pressure before the gas flow reaches the gas sensor, a flow adjustment device to adjust a flow rate of the gas flow to a standardized flow rate before the gas flow reaches the gas sensor, and a controller for receiving the electrical signal from the gas sensor and processing the electric signal to calculate the concentration of the selected gas in the gas flow.

However, such prior art solutions are not considered capable of measuring both gas concentration and gas flow-rate within a same device, particularly for low-flows inherent to ambient ground gas applications described herein. This is because the action of measuring ambient ground gas concentration can itself affect the measurement of ambient ground gas flow, and reciprocally: the measurements are said to cross-interfere with one another.

When measuring gas flow, a path is created to the open atmosphere, which allows gas in the ground-gas monitoring point to flow naturally within the path, from which to sample and measure ground gas processes in the representative location. But the open path to the open atmosphere may cause a change in the composition of the gas therein, since the air within the path may have a diluting effect on the gas. Moreover, if only a small amount or volume of gas is present in the path or sample, as is common with ground gas processes, then whichever gas is present in the path may be partly or fully evacuated by the airflow within the path, whereby measuring the gas concentration subsequently to measuring the gas flow would produce an artificially low concentration measurement.

In a working example, a device samples from a representative monitoring location, typically a borehole well with perforated sections underground and a sealed headspace. Additionally, the performance of the borehole well needs to be accounted for in consequent data collection, whereby non-sealed headspace can lead to erroneously low readings, while gastight yet infrequently perturbed well spaces can lead to artificially high readings due to gas accumulation and pressure build-up.

Conversely, when measuring gas concentration, the gas must be pumped from the sampling location for a specified time, known to the skilled person as the 'pump time', into the instrument in order to get a representative reading. This pumping action artificially changes the natural flow rate of air and gas in the device, whereby measuring the gas concentration prior to measuring the gas flow would produce an artificially high gas flow result.

Thus, to accurately measure both concentration and flow of ground gases, two separate devices are still typically used, one or both of which may be manually configured, calibrated and/or operated to attenuate or mitigate the cross interference issue, and which therefore makes high frequency monitoring unnecessarily cumbersome and onerous.

An improved solution is required, to mitigate the disadvantages of the prior art. In particular, an improved gas sensing device is required, which does not require manual data connection, dedicated manual adjustments and/or physical interchanging of connections on-site.

SUMMARY

The present invention, as set out in the appended claims, overcomes the disadvantages associated with the prior art of reference by providing a distributed ambient ground gas monitoring system including an ambient ground gas sensing device capable both of measuring both gas concentration and low magnitude gas flow-rates at high frequency, and of overcoming the cross interference issue through remote tuning of its measuring parameters.

According to an aspect of the present invention therefore, there is provided an ambient ground gas sensing device, comprising a power source, data processing means and memory means operably interfaced with the data processing means and for storing sampling configuration data and sensed data. The device further comprises sensing means operably interfaced with the power source and the data processing means, wherein the sensing means is adapted to sample ambient ground gas from a representative location according to first sampling configuration data and to output sensed gas concentration data and sensed gas flow data. The device further comprises a telemetry module operably interfaced with the power source and the data processing means, wherein the telemetry module is adapted to establish a network connection with a remote terminal, communicate the sensed data to the remote terminal and receive second sampling configuration data from the remote terminal for updating the first sampling configuration data. The sampling configuration data comprises data representative of a frequency and duration of gas flow measurement, data representative of a frequency and duration of gas concentration measurement, and data representative of an offset time corresponding to a time interval between a gas flow measurement and a gas concentration measurement.

Advantageously, the device of the invention is capable of measuring both ambient ground gas concentration and ambient ground gas flow from representative locations, and the telemetry module interfaces the device with a remote terminal for bilateral data communication, including the reporting of sensed ambient ground gas concentration and flow data reported to the user terminal and, importantly, the receiving of alternative sampling configuration parameters when the sensed data indicates cross interference between the measurements. A user of the device, or of several such devices, connected to the terminal can thus increase and maintain the accuracy of the ambient ground gas concentration and gas flow measurements without visiting the or each ambient ground gas sensing device.

In an embodiment of the device, the sensing means comprises a gas concentration sensing module and a gas flow sensing module.

An embodiment of the gas concentration sensing module may comprise a gas sampling circuit, extending between a first gas inlet and a first gas outlet and include a sensor chamber, a pump and a pressure gauge. In a variant of this embodiment, the sensor chamber and the pressure gauge may input data to a sensor circuit interfaced with the data processing means.

An embodiment of the gas flow sensing module may comprise a gas sampling circuit, extending between a second gas inlet and a second gas outlet and including a valve and a flow sensor. In a variant of this embodiment, the flow sensor may be interfaced with the data processing means.

In an embodiment of the device, the gas that is sensed is selected from methane ($CH_4$), carbon dioxide ($CO_2$), oxygen ($O_2$).

In an embodiment of the device, the sensing means may be further adapted to sense and output data representative of temperature in the range −20 to 50 degrees centigrade, and/or humidity data in the range 0% to 100% RH, and/or atmospheric pressure in the range up to 150 millibars or in the range 800 to 1200 hectopascals. Furthermore, additional sensing capacity can be integrated for measuring trace gases such as carbon monoxide (CO), hydrogen sulphide ($H_2S$) and volatile organic compounds (VOCs).

In an embodiment of the device, the power source may be a renewable energy source. In a variant of this embodiment, the power source may be power storage means interfaced with the renewable energy source. In a preferred embodiment of the device, the renewable energy source is a photovoltaic array secured to the gas sensing device. These embodiments advantageously confer a high degree of autonomy to the device, obviating the requirement for a mains connection and the associated dependency for its continuity of operation.

In an embodiment of the device, the telemetry module may be a cellular telemetry (e.g. GSM, 3G, 4G) communication circuit. This embodiment advantageously confers a still high degree of autonomy to the device, obviating the requirement for a wired network connection and the associated cabling and earthworks at installation time. In particular, when this cellular telemetry embodiment should be combined with the adjunction of a renewable power source charging a device power storage, the resultant device is fully autonomous, self-contained and capable of continuous operation, i.e. continuous sensing, sensed data communicating and sampling configuration data receiving, whether in real-time or according to a power-optimising batching strategy.

An alternative embodiment of the device may further comprise short-range wireless data networking means, for instance a Bluetooth® or RFID module facilitating bilateral data communication with another gas sensing device within radio-communication range, with a diagnostic tool of a maintenance operator, and the like.

According to another aspect of the present invention, there is also provided a gas monitoring system, comprising at least one gas sensing device according to any of the embodiments introduced above and described herein, and at least one data processing terminal having networking means, wherein the or each data processing terminal is remote from the or each gas sensing device, and the or each terminal is adapted to receive sensed gas concentration data and sensed gas flow data from the or each remote gas sensing device, and to generate device-respective second sampling configuration data according to the received sensed data for updating the first sampling configuration data at the or each remote gas sensing device.

In an embodiment of the system, the data processing terminal may be further adapted to determine an accuracy characteristic of the received sensed data and to generate the second sampling configuration data according to the determined accuracy characteristic. Advantageously, this embodiment automates the optimisation of the sensing accuracy of at least one remote gas sensing devices. Moreover, by removing the time-consuming requirement for a user to monitor and analyse the sensed data at the terminal and, as the case may warrant, input updating sampling configuration parameters at the terminal, this embodiment speeds up this optimisation, down to machine processing and network latency periods.

In an embodiment of the system, the data processing terminal may be further adapted to generate a secure user interface for output to a display, and to output graphical data representative of the received sensed gas concentration data and sensed gas flow data in the secure user interface.

In an embodiment of the system, the data processing terminal may be further adapted to generate an alert according by comparing the sensed gas concentration data and/or the sensed gas flow data against a predetermined threshold. Advantageously, this embodiment automatically alerts a user of the system about gas concentration levels in the vicinity of a gas sensing device reaching a hazardous threshold.

In an embodiment of the system, the data processing terminal may be further adapted to receive or determine a geographical location of one or more remote gas sensing devices, to correlate the or each respective geographical location with cartographical data, and to output graphical data representative of the geographical location of the or each remote gas sensing device in the user interface. Advantageously, this embodiment allows a user of the system to map both gas concentration and gas flow measurements over an area and to correlate abnormally high or hazardous readings to geographical features.

In a preferred embodiment of the system, at least one data processing terminal is a Supervisory Control and Data Acquisition ('SCADA') terminal, or part of a SCADA system. This embodiment advantageously maximises the compatibility of the gas sensing device output with legacy plant or installation data processing systems, networks and software.

In another embodiment there is provided a method to measure ambient ground gas using a sensing device, said method comprising:
  sensing sample ambient ground gas adjacent the device according to a first sampling configuration data and to output at least sensed gas concentration data and sensed gas flow data;
  communicating the sensed data to a remote terminal and receive at the sensing device second sampling configuration data from the remote terminal for updating the first sampling configuration data;
  wherein the sampling configuration data comprises data representative of a frequency and duration of gas flow measurement, data representative of a frequency and duration of gas concentration measurement, and data representative of an offset time corresponding to a time interval between a gas flow measurement and a gas concentration measurement.

According to yet another aspect of the present invention, there is also provided a computer program product, comprising a computer usable medium having a computer readable program code embodied therein, said computer readable program code adapted to be executed by a data processing terminal with networking means for configuring the terminal to receive sensed gas concentration data and sensed gas flow data from one or more remote gas sensing devices, and to generate sampling configuration data according to the received sensed data for updating sampling configuration data at the, or each, remote gas sensing device.

Other aspects of the present invention are as stated in the appended claims.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE DRAWINGS

Figure 1:
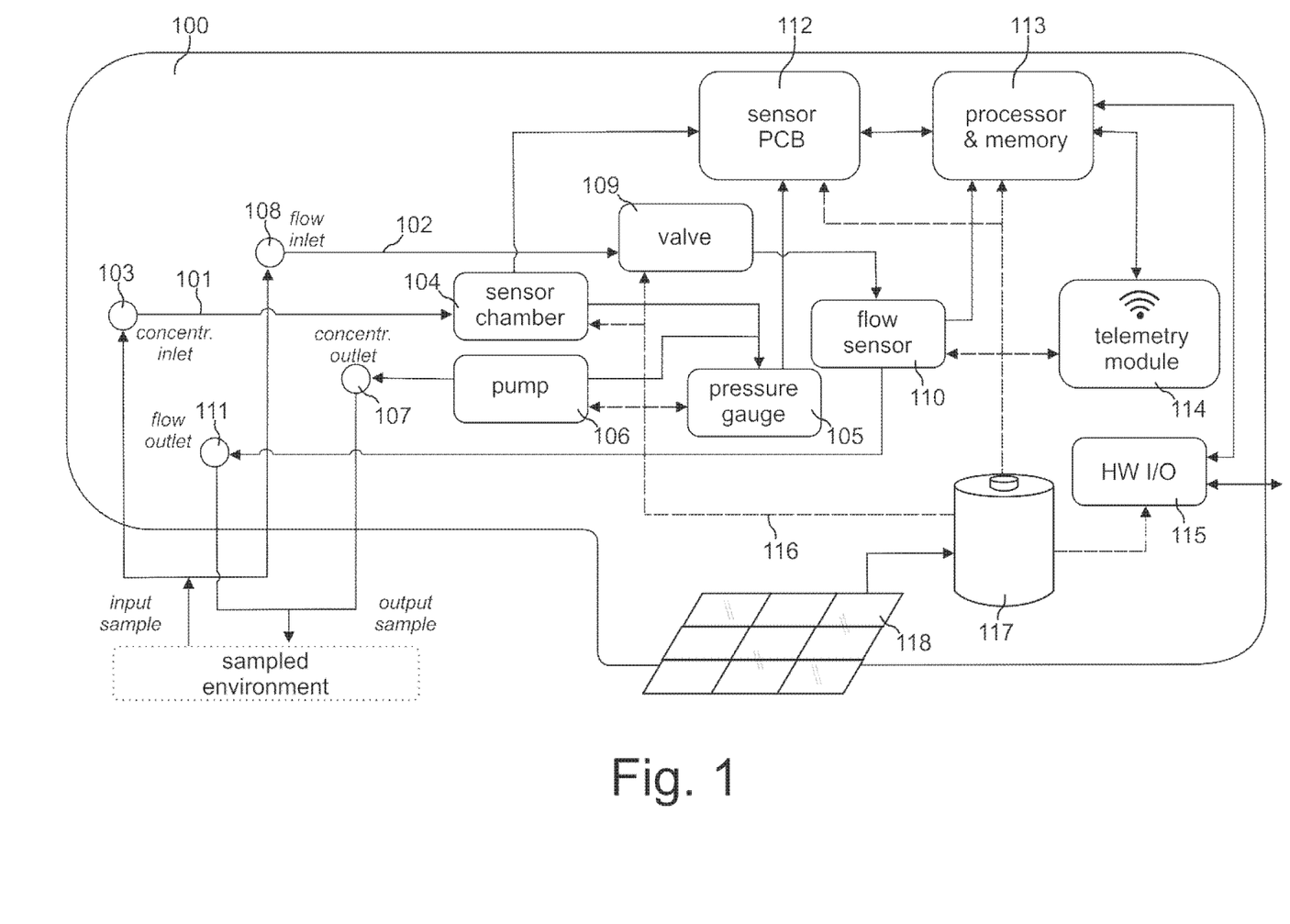
FIG. 1 illustrates the architecture of an embodiment of a gas sensing device according to the invention, including device memory means.

Referring now to the figures and initially FIG. 1, there is shown an embodiment of a self-contained and autonomous gas sensing device 100 according to the invention, adapted to sample ambient gas within its environment to sense and measure the flow and concentration of one or more gases therein, for instance one or any of methane ($CH_4$), carbon dioxide ($CO_2$), oxygen ($O_2$) or the like.

The device 100 is configured with a gas concentration sensing module and a gas flow sensing module. In this embodiment, the gas concentration sensing module comprises a first gas sampling circuit 101 for measuring a gas concentration and the gas flow sensing module comprises a second gas sampling circuit 102 for measuring a gas flow.

The first gas sampling circuit 101 comprises ducting extending from a first gas inlet 103 towards a sensor chamber 104, an output of which is in fluid communication with a pressure gauge 105. A pump 106 is in fluid communication with the first circuit ducting at a position intermediate the sensor chamber output and the pressure gauge input. The first gas sampling circuit 101 is completed by a first exhaust outlet 107 in fluid communication with an output of the pump 106.

The second gas sampling circuit 102 comprises ducting extending from a second gas inlet 108 towards a valve 109, an output of which is in fluid communication with a flow sensor 110. The second gas sampling circuit 102 is completed by a second exhaust outlet 111 in fluid communication with an output of the flow sensor 110.

The first and second gas sampling circuits 101, 102 are distinct from one another between their respective inlets 103, 108 and outlets 107, 111 and thus define two distinct gas flow passages within the device 100, whereby ambient gas samples for measuring gas concentration are kept distinct from ambient air samples for measuring gas flow.

The sensor chamber 104 and the pressure gauge 105 of the first circuit 101 respectively output sensed gas data and sensed pressure data as electrical signals to a sensor module 112, in the example a sensor printed circuit board (PCB) 112, at which the gas concentration is calculated. The sensor PCB 112 outputs calculated gas concentration data to a device controller module 113, comprising a central processor unit ('CPU') and memory means, in the example non-volatile random access memory ('NVRAM'). The datalink between the sensor PCB 112 and the controller 113 is bidirectional, whereby configuring and updating data for the operating parameters of the sensor PCB 112 may be received from the controller 113. The flow sensor 110 of the second circuit 102 outputs sensed gas flow data as electrical signals to the device controller module 113.

The sampling frequency of the device 100 is fully adjustable by the device controller module 113, and the sensing characteristics of the first and second circuits controlled by the controller 113 provide a capacity to sense methane ($CH_4$) and carbon dioxide ($CO_2$) and calculate either concentration from 0 to 100 volume/volume percent; a capacity to sense oxygen ($O_2$) and calculate its concentration from 0 to 25 volume/volume percent; a capacity to sense carbon monoxide (CO) and calculate its concentration from 0 to 1,000 part per million; a capacity to sense and measure ambient temperature in the range −20 to 50 degrees centigrade; a capacity to sense and measure relative humidity (RH, non-condensing) in the range 0% to 100%; a capacity to sense and measure atmospheric pressure in the range up to 150 millibars or in the range 800 to 1200 hectopascals (hPa); and a capacity to sense and measure gas flow through thermal mass flow measurement principles and output same as a sl/hr (standard litres per hour).

The device controller module 113 thus outputs calculated sensed gas concentration data and calculated sensed gas flow data to a telemetry module 114, in the example a mobile telephony PCB conforming to the Global System for Mobile Communications GSM ('GSM') standard or subsequent cellular telemetry standards (third-generation 3G or fourth-generation 4G), chosen for its low power requirement and robustness. The datalink between the CPU controller 113 and the telemetry module 114 is bidirectional, whereby configuring and updating data for the respective operating parameters of the controller 113 and the sensor PCB 112 may be received through the telemetry module 114 over the air.

For redundancy of operation and ad hoc local maintenance purposes, the device 100 further comprises a universal serial bus ('USB') input/output interface 115 in bidirectional data communication with the controller 113, wherein the calculated sensed gas concentration data and calculated sensed gas concentration data may also be output to a local storage device connected to the interface 115, and wherein configuring and updating data for the respective operating parameters of the controller 113 and the sensor PCB 112 may likewise be received locally the USB interface 115, either from the local storage device or as user input data input through a HiD device alternatively connected to the interface 115.

The active components 104-106, 109-110 and 112-115 of the device 100 are connected to a power bus 116, shown in dotted line in the Figure, which is supplied by a battery 117, wherein the battery is charged by a solar photovoltaic array 118. The solar PV array may be suitably sized for either securing to the body of the device 100 or, at any rate, so as to be not significantly larger than the body of the device 100, and so improve the portability of the autonomous gas sensing device 100. An embodiment of the gas sensing device 100 is self-contained within an body conforming to level 66 of the International (or Ingress) Protection standard (IEC standard 60529), having overall dimensions of 360× 220×200 millimeters and a total weight of 2,4 kilograms, which is suitable for temporary or permanent locating on borehole wells, manifolds or pipes.

Specific details such as the battery type or capacity, the presence of an inverter intermediate the battery 117 and the solar PV array 118, and the like are considered to be straightforward implementation details for the skilled reader, and have thus been omitted for the purpose of not obscuring the present description unnecessarily, and it will be readily understood that the device architecture 100 shown in FIG. 1 and described herein will be capable of variation and optimization without departing from the scope of the invention as claimed herein.

Figure 2:
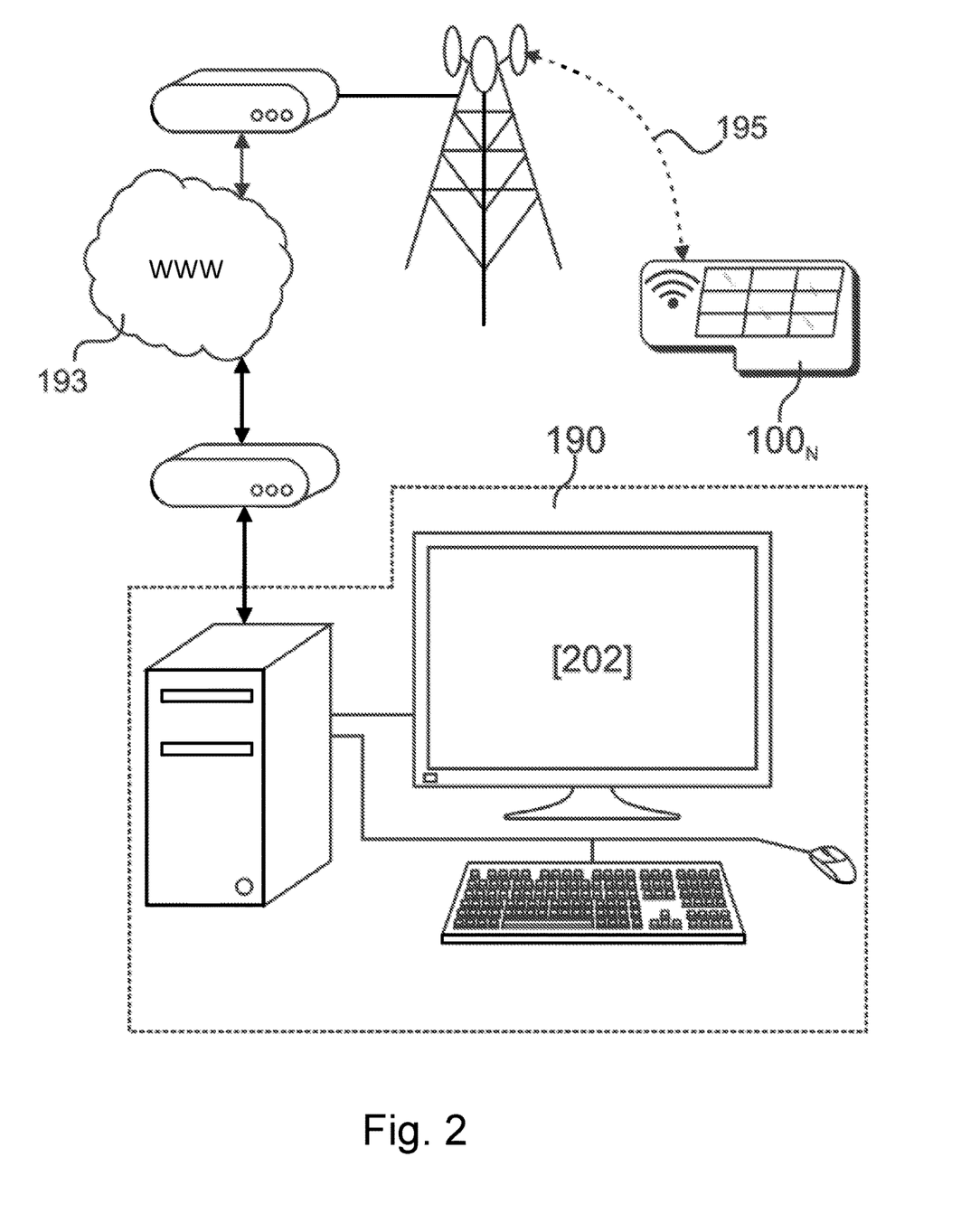
FIG. 2 shows an embodiment of a system for remotely monitoring gas according to the invention using the gas sensing device of FIG. 1 and a data processing terminal, including terminal memory means.

With reference to FIG. 2 now, an embodiment of the gas monitoring system according to the invention is shown, which includes at least one data processing terminal 190 and at least gas sensing device 100 remote from the terminal 190, wherein a networked data connection can be established and maintained between the terminal 190 and the device 100. It will be readily understood by the skilled reader from the foregoing, that the system may include any number N of further gas sensing devices 100, each with a respective networked data connection established and maintained with the terminal 190, or any number N of further terminals 190. The terminal 190 can communicate over a network, for example over an internet connection 193 or other communication means.

The telemetry module 114 provides the gas sensing device 100 with mobile telephony functionality, effectively configuring the gas sensing device 100 as a telemetry communication device whenever the telemetry module 114 is invoked by the device controller 113. Accordingly, the device 100 emits and receives data, in the example emitting alphanumerical data representative of sensed gas data and receiving alphanumerical data representative of sampling configuration parameters, wherein these communications are encoded as digital signals over a wireless data transmission 195, or other transmission means.

Accordingly, network connectivity and interoperable networking protocols of the or each terminal $190_N$ and the or each gas sensing device $100_N$ allows a terminal 190 and a gas sensing device 100 to connect to one another, and both communicate data to and receive data from, one another according to the methodology described herein.

A typical hardware architecture of the terminal 190 is also shown in FIG. 2 in further detail, by way of non-limitative example. As skilled persons will readily understand, the hardware architecture of the terminal 190 may vary substantially, depending upon whether the terminal is a desktop computer as per the example herein, or an alternative personal computing device, particularly a portable device such as a tablet computer or a mobile telephone handset, which are considered equally apt to embody the terminal of a system according to the invention.

Figure 3:
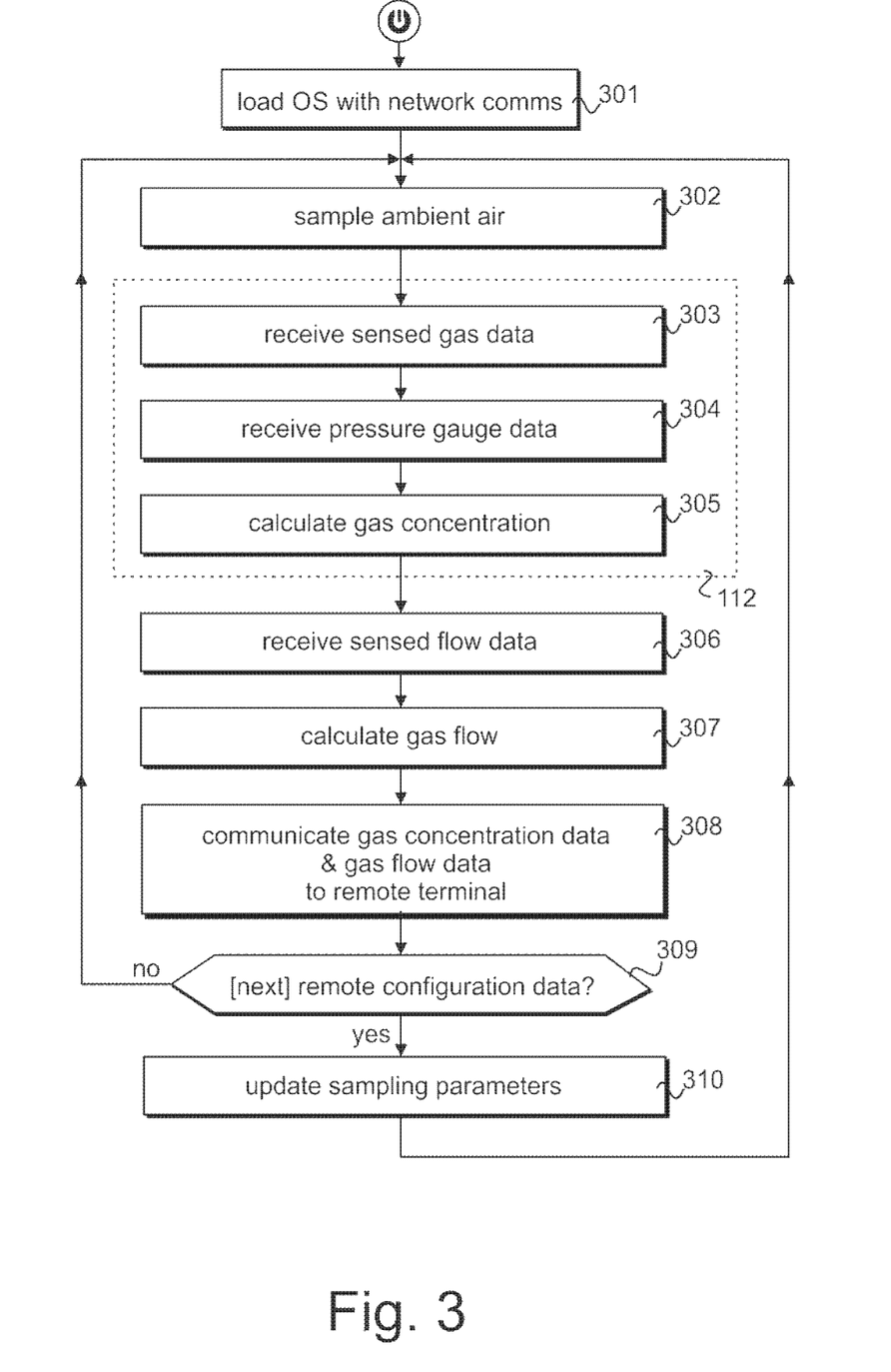
FIG. 3 illustrates gas sensing and data processing steps performed by the gas sensing device of FIGS. 1 and 2.

Within the context of the system shown in and described with reference to FIGS. 1 and 2, the methodology of the invention is implemented as a data processing logic processed at each of a gas sensing device 100 and a terminal 190 for monitoring gas in the vicinity of the gas sensing device 100, and the logic processed at the gas sensing device 100 is now described with reference to FIG. 3. Data processing steps of the methodology are described as a discrete group of chronological data processing tasks repeated iteratively at runtime.

After powering up the gas sensing device 100 conventionally, an operating system ('OS') is loaded into the device memory 113 and started locally at step 301, including device component driving subroutines for controlling the PCB 112 and the telemetry module 114 and communications subroutines implementing network interoperability through the telemetry module 114.

Ground-gas adjacent the gas sensing device 100 is next sampled at step 302, according to default or first sampling configuration parameters configuring the operation of each of the sampling circuits 101, 102 and the PCB 112. Sampling configuration parameters considered critical to measure accurately both gas concentration and flow generally include frequency and length of gas flow measurements, frequency and length of concentration measurements, and an offset time. Sampling configuration parameters should also preferably include pump time.

The frequency and length of gas flow measurements relate to the quantity of flow samples that can be taken in a given period to maximise gas flow data gathering, however affecting a subsequent measurement of gas concentration, by allowing gas to escape the well 111.

The frequency and length of gas concentration measurements relate to the quantity of samples that can be taken in a given period to maximise gas concentration data gathering, however prior to frequently pumping the gas, since this artificially changes the natural flow rate in the adjacent well 108 and thus reduces the accuracy of the flow measurements.

The offset time is a time interval between gas flow measurements and gas concentration measurements, considered sufficient to allow gas in the environment adjacent the device 100 to settle back to a normal behaviour after a first measurement, which thus further mitigates the potential for cross-interference between the measurements.

The pump time relates to the length of time during which gas is pumped from the well 103 into the device to ensure that a representative sample is in the chamber 104 when measuring gas concentration.

Default sampling values for at least the frequency and length of gas flow measurements, the frequency and length of gas concentration measurements and the offset time are encoded in the device 100 at the time of manufacture and/or of commissioning of a device 100 on-site, which may be the sampling configuration parameters used at the first instantiation of a step 302 further to powering up the device 100. In embodiments of the device and system, the pump time may also be included in the default sampling values, and higher sampling frequencies may be preferred to improve accuracy of the sensed data through volume of samples.

At step 303, the PCB 112 receives the sensed gas data from the chamber 104. At step 304, the PCB 112 receives the sensed pressure data from the gauge 105. At step 305, the PCB 112 calculates a gas concentration measurement based on the received sensed gas data and the received pressure data, and outputs the gas concentration measurement to the controller 113.

After an offset time period, at step 306 the controller 113 receives the sensed gas flow data from the flow sensor 110. At step 307, the controller 113 calculates a gas flow measurement based on the received sensed gas flow data. At step 308, the controller 113 processes the gas concentration measurement of step 305 and the gas flow measurement of step 306 into network data packets addressed to the remote terminal 190, and invokes the telemetry module 114 to communicate the data packets to the remote terminal 190.

Due to the tendency for ground gas to fluctuate in the environs and, moreover, as the more samples are taken, the more likely measurements are to cross-interfere, the default or current configuration parameter values may need to change if and as the gas behaviour changes. The telemetry module 114 of the gas sensing device 100 assists this requirement, by transmitting the data generated from the measurement to the remote terminal 190 for analysis and receiving updating configuration parameter values if the analysis indicates that cross-interference is occurring and/or that the gas behaviour is changing. The telemetry module 114 thus makes it possible to manage the monitoring performance of the device 100 remotely and, if required, to effect changes to the sampling parameters for improving the accuracy of measurement.

Accordingly, a question is subsequently asked at step 309, about whether one or more new values for one or more of the sampling configuration parameters have been received from the remote terminal 190 through the telemetry module 115. If the question step 309 is answered negatively, the control logic returns to the step 302 of sampling, which is accordingly performed with the current sampling configuration parameters, being those same as used for the immediately-preceding instantiation of step 302, whereby a next gas concentration measurement and a next gas flow measurement are calculated according to steps 303 to 307 and communicated to the remote terminal 190 at step 308, and so on and so forth.

Alternatively, if the question of step 309 is answered negatively, then at step 310 the current value or values for the one or more of the sampling configuration parameters in the controller memory 113 is updated with the corresponding value received from the remote terminal 190. The control logic then returns to the step 302 of sampling, which is accordingly performed with the updated sampling configuration parameters, whereby a next gas concentration measurement and a next gas flow measurement are calculated according to steps 303 to 307 based on the updated sampling configuration, and communicated to the remote terminal 190 at step 308, and so on and so forth.

Figure 4:
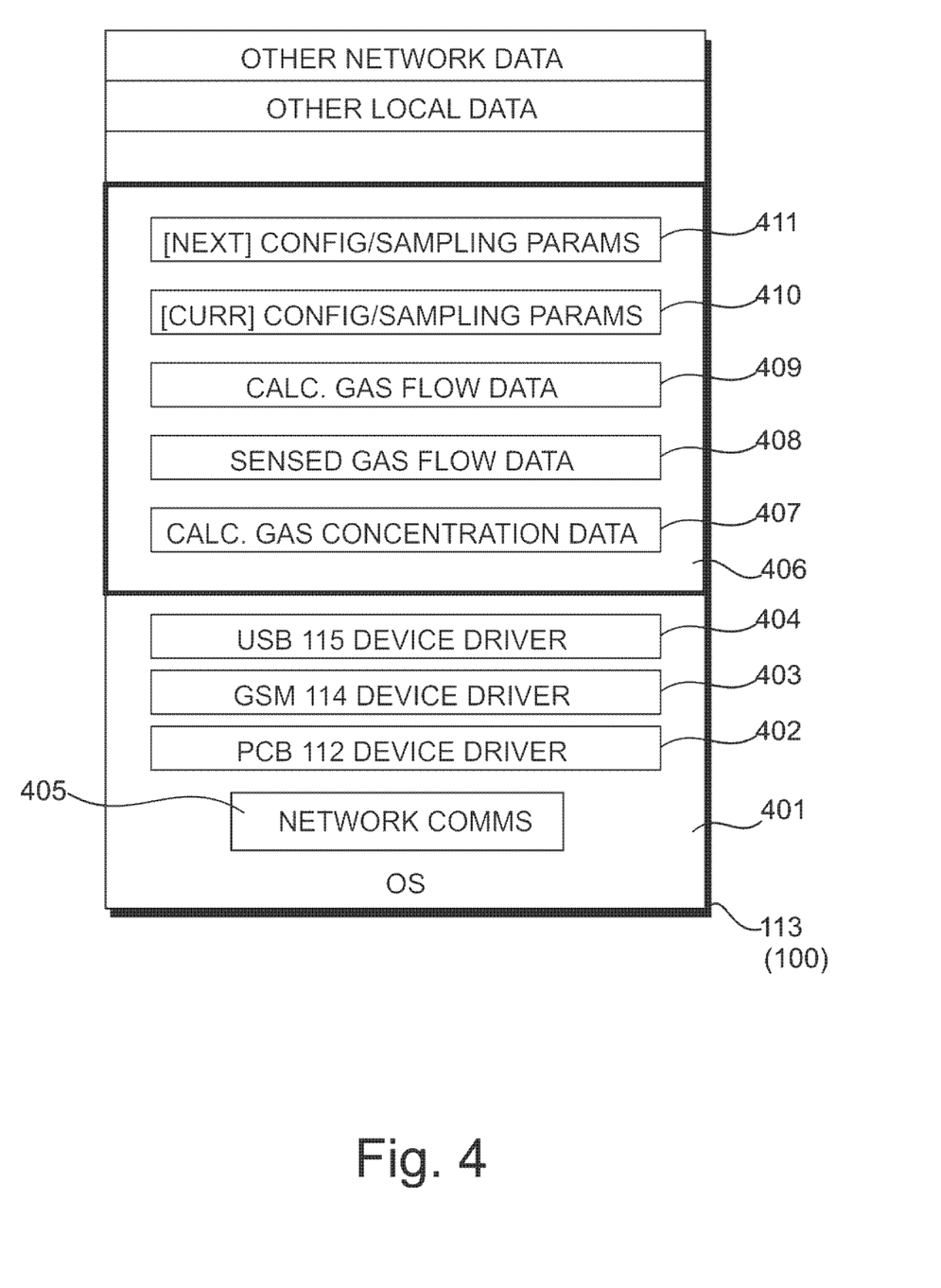
FIG. 4 shows the contents of the memory means of the device of FIG. 1, when the gas sensing device performs the steps of FIG. 3.

In one embodiment the contents of the memory means 113 of the device 100 at runtime, when steps 301 to 310 are processed by the CPU 113, are illustrated in FIG. 4, wherein the operating system loaded at step 301 is shown at 401 which, if the controller 113. The Operating System 401 includes instructions for governing the basic data processing, interdependence and interoperability of the device hardware components such as, with reference to FIGS. 1 and 3 and their description herein, device drivers 402, 403, 404 respectively for the sensor PCB 112, the telemetry module 114 and the USB interface 115, and communication subroutines 405 to configure the controller 113 for network communication with the remote terminal 190 via the telemetry module 114.

The device controller 113 is configured to perform steps 305 to 310 by a set of instructions 406 residing in the memory means at runtime. The set of instructions 406 can be interfaced with the OS 401 through one or more Application Programmer Interfaces (API). Calculated gas concentration data received from the PCB 112 is shown at 407, gas flow measurement data from the flow sensor 109 is shown at 408 and calculated gas flow data is shown at 409. The current sampling configuration parameters according to which sampling is performed a step 302 are shown at 410 and updating sampling configuration parameters received from the remote terminal 190 according to which sampling will be performed at a next step 302 are shown at 411.

The memory means 113 may include further data which is not associated with steps 302 to 310 of the gas monitoring application 406, including local and network data, for instance a set of updating instructions for the OS 401 received either locally from a mass storage device connected to the USB interface 115 or remotely over the air through the telemetry module 114.

Figure 5:
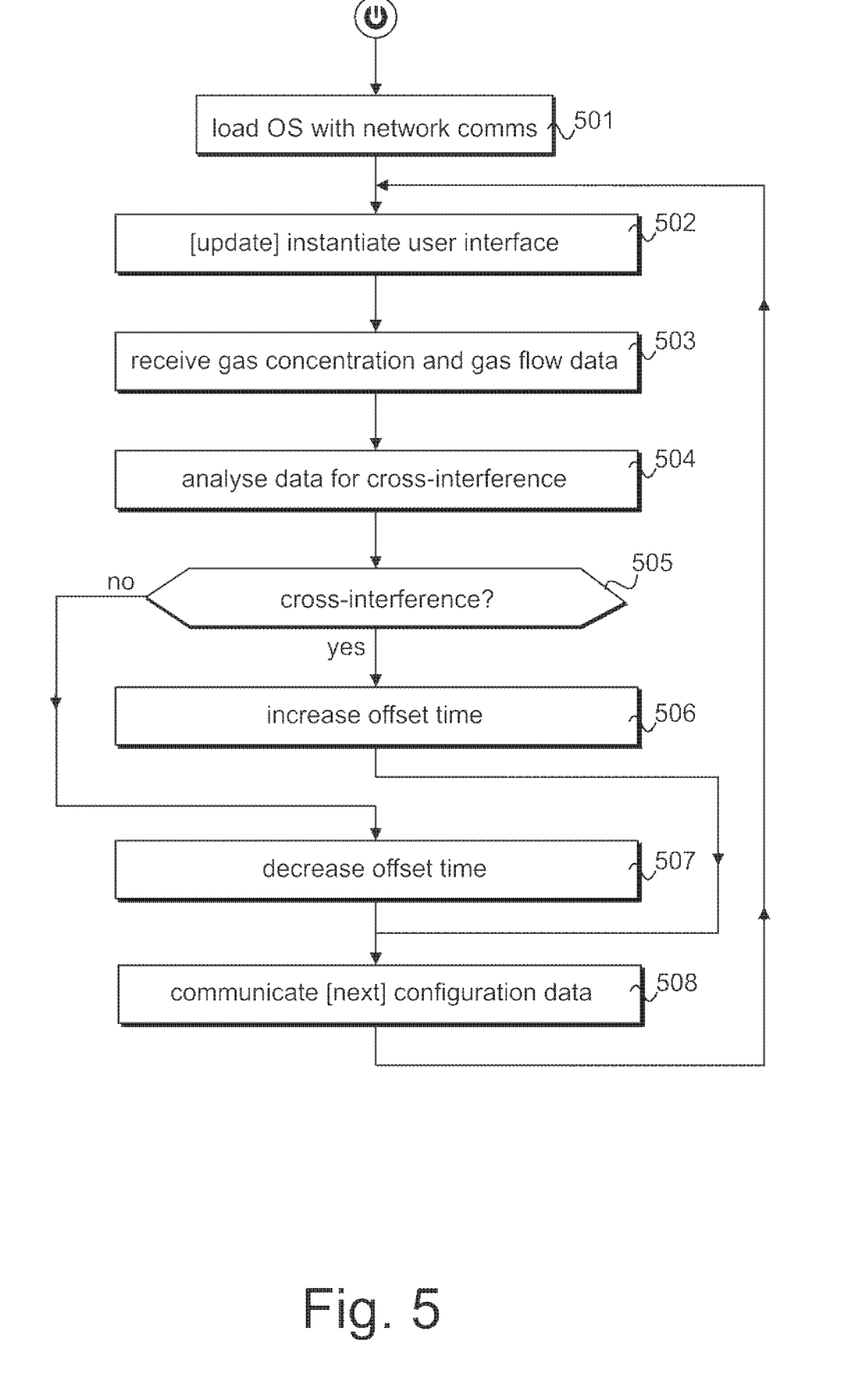
FIG. 5 illustrates data processing steps performed by the terminal of FIG. 2.

Within reference again to the context of the system shown in FIGS. 1 and 2, further to describing the methodology of the invention implemented as a data processing logic processed the gas sensing device 100 as shown FIG. 5, the logic processed at the terminal 190 is now described with reference to FIG. 5. Data processing steps of the methodology are again described as a discrete group of chronological data processing tasks repeated iteratively at runtime.

After powering up the terminal 190 conventionally, an operating system ('OS') is loaded into the device memory 209 and started locally at step 501, including device component driving subroutines for controlling the NIC 211 and communications subroutines implementing network interoperability through the NIC 211.

At step 502, a gas monitoring application is started, which instantiates a user interface and outputs same to the VDU 202 for facilitating the display of received gas concentration and gas flow measurements to a user, and the input of updating sampling configuration parameters for one or more remote gas sensing devices $100_N$. At step 503, calculated gas concentration data 407 and calculated gas flow data 409 is received from a remote gas sensing device 100 across the network 193. The received gas data is next analysed for cross-interference at step 504 with a suitable subroutine at step 504.

A question is accordingly asked at step 505, about whether the received concentration and flow data is representative of cross-interference occurring at the gas sensing device 100. If the question of step 505 is answered positively, then at a next step 506, the sampling configuration parameters are altered to reduce the likelihood of cross-interference on a next sampling operation of the gas sensing device 100. For instance, the offset time parameter may be increased by a predetermined interval or unit.

Alternatively, when the question of step 505 is answered negatively, then the absence of cross-interference is considered representative of unused monitoring capacity, and the sampling frequency of the gas sensing device 100 is increased at a next step 507 by decreasing the offset time parameter by a predetermined interval or unit, such that a next sampling operation of the gas sensing device 100 should result in faster-measured gas concentration and gas flow, eventually resulting in more data from the upcycled device 100 increasing the accuracy of the gas monitoring through statistical volume.

Thus, following from either step 506 or step 507, the gas monitoring application communicates the updating sampling configuration parameter, comprising either the increased offset time or the decreased offset time, to the remote gas sensing device 100 at step 508.

The control logic then returns to the step 502 of instantiating the user interface, wherein the second and any subsequent such step 502 updates the contents of the user interface with calculated gas concentration data 407 and calculated gas flow data 409 received from the same $100_1$ or another $100_2$ remote gas sensing device across the network 193, which may then be analysed at step 504 and the sampling configuration parameters of the same or different gas sensing device $100_1$, $100_2$ updated per steps 505-508, and so on and so forth.

Figure 6:
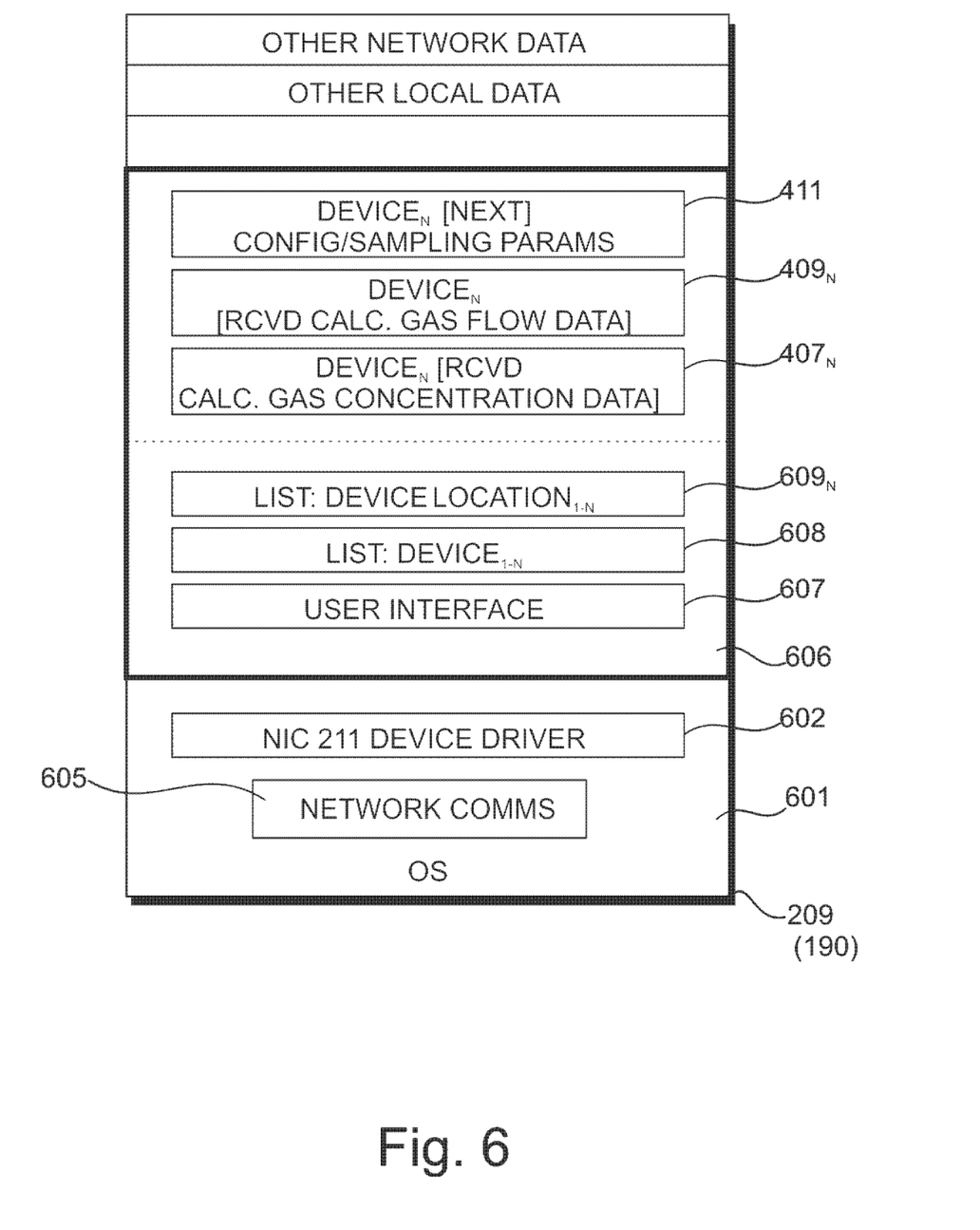
FIG. 6 shows the contents of the memory means of the terminal of FIG. 2, when the terminal performs the steps of FIG. 5.

The contents of the memory means of the terminal 190 at runtime, when steps 501 to 508 are processed by a CPU, are illustrated in FIG. 6, wherein the operating system loaded at step 501 is shown at 601 which, if the terminal 190 is a desktop computer. The OS 601 includes instructions for governing the basic data processing, interdependence and interoperability of the device hardware components, including a device driver 602 for a NIC module 211, and communication subroutines 605 to configure the terminal 190 for network communication with the remote gas sensing devices $100_N$.

The terminal 190 is configured to perform steps 502 to 508 by a set of instructions 606 residing in the memory means at runtime. The set of instructions 606 is interfaced with the OS 601 through one or more Application Programmer Interfaces (API) and the user interface instantiated at step 502 is shown at 607. The user interface 607 is a secure user interface, wherein the gas monitoring application 606 requires a user to first provide authentication before outputting received gas measurements and accepting input from HiD devices therein.

A list 608 is maintained by the gas monitoring application 606 of the one or more gas sensing devices $100_N$ in use, from which calculated gas concentration data and calculated gas flow data may be received at step 503. The application 606 is adapted to correlate gas sensing device location with cartographical map data and therefore stores the respective location coordinates $609_N$ of each gas sensing device $100_N$ in the list 608. The user interface 607 is adapted to output the correlated location on map data, for instance through a Google Map® applet or plug-in as provided by Google, Inc.

The respective calculated gas concentration data and calculated gas flow data received from each gas sensing device $100_N$ is shown at $407_N$, $409_N$ respectively, and the updating sampling configuration parameter generated according to steps 505-507 for network packet encoding at step 508 is shown at 411.

The memory means may again include further data which is not associated with steps 502 to 508 of the gas monitoring application 606, including local and network data, for instance and respectively user input data received and a set of updating instructions for the OS 601 received over the network.

According to the invention therefore, a gas sensing device 100 is provided, which incorporates gas concentration and flow sensing modules and which also includes a telemetry module, used to transmit the dataset generated from measuring the gas concentration and gas flow to a remote terminal. These measurements can then be analysed to detect for cross interference, and adjustments can be made to both measurement routines for reducing the cross interference effect.

By providing a device which operates autonomously, is IoT-enabled and which is capable of measuring both gas concentration and gas flow at high frequency, it is possible to quickly obtain large datasets, which themselves enable a very accurate understanding of gas processes under measurement, moreover substantially real-time. As such, the system of the invention may be particularly suited to circumstances wherein ground gas measurements are routinely conducted, such as landfill risk assessments and surrender applications, contaminated land assessment for ground gas and soil vapour, fracking and other unconventional oil and gas environmental risk assessments.

Generally, the gas sensing device 100 of the invention is intended to analyse gas and air quality levels across a wide range of environments, variously including coal mines and other mines, oil and gas extraction installations, refineries, landfills, contaminated areas and even generic public areas. In all such contexts, the gas sensing device 100 of the invention is intended to provide, or otherwise assist with, a wide variety of applications, variously including monitoring anaerobic digestion; monitoring indoor and/or outdoor air quality; remotely monitoring unmanned locations, understanding modelling and predicting gas behaviour; detecting and preventing unwanted gas migration; accelerate site remediation; and more.

In particular, an important current issue in the contaminated land industry is over-engineering solutions for mitigating ambient ground gas risk. Until the monitoring device 100 and system of the present invention, it has not been practical to measure ambient ground gas flow-rate & concentration continuously, whereby the industry still routinely adopts a worst-case approach: a reading from a prior art handheld device is assumed to represent the constant behaviour of the gas, whereby a sampler recording high readings therefore produces a high risk assessment necessitating considerable ambient ground gas protection measures. Because samplers are encouraged by normative regulations to take samples when climatic conditions are more likely to produce high readings, the likelihood of generating a high risk assessment is correspondingly high and there is a common perception in the contaminated land industry that over-engineering of gas-mitigation solutions in response to artificially-high risk assessments is very common. The gas sensing device 100 and system of the invention is intended to allow the contaminated land industry to perform more accurate risk assessments of ambient ground gas, in the expectation of developing more efficient and economical mitigating solutions.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A gas sensing device to measure ambient ground gas, comprising:
    a power source;
    a data processor;
    a memory operably interfaced with the data processor and for storing sampling configuration data and sensed data;
    a sensor operably interfaced with the power source and the data processor and comprising a gas concentration sensing module and a gas flow sensing module, wherein the sensor is adapted to sample ambient ground gas adjacent the device according to first sampling configuration data and to output at least sensed gas concentration data and sensed gas flow data, wherein the gas concentration sensing module comprises a first gas sampling circuit, extending between a first gas inlet and a first gas outlet and including a sensor chamber, a pump and a pressure gauge and wherein the gas flow sensing module comprises a second gas sampling circuit extending between a second gas inlet and a second gas outlet and including a valve and a flow sensor; and
    a telemetry module operably interfaced with the power source and the data processor, wherein the telemetry module is adapted to establish a network connection with a remote terminal, communicate the sensed data to the remote terminal and receive second sampling configuration data from the remote terminal for updating the first sampling configuration data,
    wherein the sampling configuration data comprises data representative of a frequency and duration of gas flow measurement, data representative of a frequency and duration of gas concentration measurement, and data representative of an offset time corresponding to a time interval between a gas flow measurement and a gas concentration measurement.

2. The device according to claim 1, wherein the gas is selected from methane ($CH_4$), carbon dioxide ($CO_2$), oxygen ($O_2$), carbon monoxide (CO), hydrogen sulphide ($H_2S$) and volatile organic compounds (VOCs).

3. The device according to claim 1, wherein the sensor is further adapted to sense and output data representative of temperature in a range −20 to 50 degrees centigrade, and/or humidity data in a range 0% to 100% RH, and/or atmospheric pressure of up to 150 millibars or in a range 800 to 1200 hectopascals.

4. The device according to claim 1 wherein the power source is a renewable energy source.

5. The device according to claim 4, wherein the power source is a power storage module interfaced with the renewable energy source.

6. The device according to claim 4, wherein the renewable energy source is a photovoltaic array secured to the gas sensing device.

7. The device according to claim 1, wherein the telemetry module is a telemetry communication circuit.

8. The device according to claim 1, wherein the gas sensing device further comprises short-range wireless data networking means.

9. An ambient gas monitoring system, comprising:
    at least one ambient gas sensing device comprising a gas concentration sensing module and a gas flow sensing module and adapted to sample ambient ground gas adjacent the gas sensing device according to first sampling configuration data; and
    a data processing terminal coupled to a network,
    wherein the data processing terminal is adapted to receive sensed gas concentration data and sensed gas flow data from the at least one remote gas sensing device, and to generate device-respective second sampling configuration data according to the received sensed gas concentration data and sensed gas flow, wherein the second sampling configuration data is used to update the first sampling configuration data at the at least one remote gas sensing device,
    wherein the gas concentration sensing module comprises a first gas sampling circuit, extending between a first gas inlet and a first gas outlet and including a sensor chamber, a pump and a pressure gauge, and
    wherein the gas flow sensing module comprises a second gas sampling circuit extending between a second gas inlet and a second gas outlet and including a valve and a flow sensor.

10. A method to measure ambient ground gas using a sensing device, said method comprising:
    sensing sample ambient ground gas adjacent the device according to a first sampling configuration data and to output at least sensed gas concentration data and sensed gas flow data, wherein the sensing device comprises a gas concentration sensing module and a gas flow sensing module; and
    communicating the sensed data to a remote terminal and receive at the sensing device second sampling configuration data from the remote terminal for updating the first sampling configuration data,
    wherein the gas concentration sensing module comprises a first gas sampling circuit, extending between a first gas inlet and a first gas outlet and including a sensor chamber, a pump and a pressure gauge,
    wherein the gas flow sensing module comprises a second gas sampling circuit extending between a second gas inlet and a second gas outlet and including a valve and a flow sensor, and
    wherein the sampling configuration data comprises data representative of a frequency and duration of gas flow measurement, data representative of a frequency and duration of gas concentration measurement, and data representative of an offset time corresponding to a time interval between a gas flow measurement and a gas concentration measurement.

* * * * *